(12) United States Patent
Zhu et al.

(10) Patent No.: US 12,680,997 B2
(45) Date of Patent: Jul. 14, 2026

(54) DETECTION SYSTEM AND METHOD, COMPUTER DEVICE, AND COMPUTER READABLE STORAGE MEDIUM

(71) Applicant: Reemoon Technology Co., Ltd., Ganzhou (CN)

(72) Inventors: Er Zhu, Ganzhou (CN); Yi Zhu, Ganzhou (CN)

(73) Assignee: Reemoon Technology Co., Ltd., Ganzhou (CN)

( * ) Notice: Subject to any disclaimer, the term of this patent is extended or adjusted under 35 U.S.C. 154(b) by 256 days.

(21) Appl. No.: 18/579,727

(22) PCT Filed: May 7, 2022

(86) PCT No.: PCT/CN2022/091409
§ 371 (c)(1),
(2) Date: Jan. 16, 2024

(87) PCT Pub. No.: WO2023/005321
PCT Pub. Date: Feb. 2, 2023

(65) Prior Publication Data
US 2024/0319159 A1     Sep. 26, 2024

(30) Foreign Application Priority Data
Jul. 30, 2021     (CN) ......................... 202110870046.9

(51) Int. Cl.
*G06T 7/11*          (2017.01)
*G01N 21/88*      (2006.01)
(Continued)

(52) U.S. Cl.
CPC ....... *G01N 33/025* (2013.01); *G01N 21/8806* (2013.01); *G01N 21/8851* (2013.01);
(Continued)

(58) Field of Classification Search
CPC ............. G01N 33/025; G01N 21/8806; G01N 21/8851; G01N 35/04; G01N 2021/8466;
(Continued)

(56) References Cited

U.S. PATENT DOCUMENTS

| | | | | |
|---|---|---|---|---|
| 2008/0079802 A1* | 4/2008 | Nilson | ................... | A61B 5/107 |
| | | | | 348/44 |
| 2011/0309004 A1* | 12/2011 | Morley | ..................... | B07C 5/36 |
| | | | | 209/577 |
| 2020/0182696 A1 | 6/2020 | Sun et al. | | |

FOREIGN PATENT DOCUMENTS

| | | |
|---|---|---|
| CN | 103234905 A | 8/2013 |
| CN | 107063129 A | 8/2017 |

(Continued)

OTHER PUBLICATIONS

International Search Report and Written Opinion mailed Jul. 18, 2022 in connection with International Application No. PCT/CN2022/091409.

(Continued)

*Primary Examiner* — Stephen P Coleman
(74) *Attorney, Agent, or Firm* — Wolf, Greenfield & Sacks, P.C.

(57) ABSTRACT

Provided are detection system and method, computer device, and computer readable storage medium; the detection system includes laser, camera unit, and computer device; the camera unit is mounted in upper region of measured object; the laser is mounted directly above the measured object, and transmitting port of the laser is facing the measured object; the laser is configured for projecting a laser plane, the laser plane intersecting surface of the measured object to form laser line, and the laser line dividing the surface into multiple different regions of interest; the camera unit is configured for collecting images of the measured object from different shooting angles, each image including part or (Continued)

all of each region of interest; and the computer device is configured for cutting and splicing all of the images based on the region of interest contained in each image to obtain target image of the surface.

15 Claims, 9 Drawing Sheets

(51) Int. Cl.

| | |
|---|---|
| *G01N 33/02* | (2006.01) |
| *G01N 35/04* | (2006.01) |
| *G06T 3/4038* | (2024.01) |
| *G06T 7/00* | (2017.01) |
| *G06T 7/73* | (2017.01) |
| *G01N 21/84* | (2006.01) |

(52) U.S. Cl.
CPC .......... *G01N 35/04* (2013.01); *G06T 3/4038* (2013.01); *G06T 7/0004* (2013.01); *G06T 7/11* (2017.01); *G06T 7/74* (2017.01); *G01N 2021/8466* (2013.01); *G01N 2021/8809* (2013.01); *G01N 2021/8864* (2013.01); *G01N 2035/0406* (2013.01); *G01N 2035/0441* (2013.01); *G06T 2200/32* (2013.01); *G06T 2207/10016* (2013.01)

(58) Field of Classification Search
CPC ... G01N 2021/8809; G01N 2021/8864; G01N 2035/0406; G01N 2035/0441; G01N 2021/8887; G06T 3/4038; G06T 7/0004; G06T 7/11; G06T 7/74; G06T 2200/32; G06T 2207/10016; G06T 7/0002; G06T 7/73
USPC ........................................................ 382/141
See application file for complete search history.

(56) References Cited

FOREIGN PATENT DOCUMENTS

| | | | |
|---|---|---|---|
| CN | 107830813 | A | 3/2018 |
| CN | 109186491 | A | 1/2019 |
| CN | 210906973 | U | 7/2020 |
| CN | 112567230 | A | 3/2021 |
| CN | 112884880 | A | 6/2021 |
| CN | 113567453 | A | 10/2021 |
| DE | 102011001127 | A1 | 9/2012 |
| DE | 102018111638 | A1 | 11/2019 |
| JP | 2005-315868 | A | 11/2005 |
| JP | 2013-231668 | A | 11/2013 |
| KR | 20200018640 | A | 2/2020 |
| WO | WO 2008/016309 | A1 | 2/2008 |

OTHER PUBLICATIONS

Chinese First Office Action dated Jun. 24, 2023 in connection with Chinese Application No. 202110870046.9.
Chinese Notification to Grant Patent Right for Invention dated Nov. 7, 2023 in connection with Chinese Application No. 202110870046.9.
Austrailian Examination Report dated Oct. 4, 2024 in connection with Austrailian Application No. 2022316746.
Brazilian Search Report and Written Opinion dated Feb. 12, 2026 in connection with Brazilian Application No. 112024000697-2.
Chilean Office Action dated May 15, 2025 in connection with Application No. CL 2024000176.
European Communication dated Oct. 14, 2024 in connection with European Application No. 22847936.6.
Extended European Search Report dated Sep. 30, 2024 in connection with European Application No. 22847936.6.
Japanese Office Action dated Jan. 6, 2026 in connection with Japanese Application No. 2024-503950.
Korean Office Action dated Nov. 20, 2025 in connection with KoreanApplication No. 10-2024-7004068.
New Zealand Examination Report dated Oct. 22, 2025 in connection with Application No. NZ 807236.

* cited by examiner

10 normal (1) the front view (2) the right view (3) the top view (1) the front view (2) the right view (3) the top view (1) the front view (2) the right view (3) the top view (1) the front view (2) the right view (3) the top view

DETECTION SYSTEM AND METHOD, COMPUTER DEVICE, AND COMPUTER READABLE STORAGE MEDIUM

CROSS-REFERENCE TO RELATED APPLICATIONS

This application is a 35 U.S.C. § 371 National Phase filing of International Application No. PCT/CN2022/091409, filed on May 7, 2022, entitled "DETECTION SYSTEM AND METHOD, COMPUTER DEVICE, AND COMPUTER READABLE STORAGE MEDIUM," which claims priority to and the benefit of Chinese patent application No. 202110870046.9, filed with the Chinese Patent Office on Jul. 30, 2021, and entitled "Detection System and Method, Computer Device, and Computer Readable Storage Medium." The contents of these applications are incorporated herein by reference in their entirety.

TECHNICAL FIELD

The present disclosure relates to the technology field of detection, specifically to a detection system and method, computer device, and computer-readable storage medium.

BACKGROUND ART

Fruits and vegetables are prone to damage during processes such as harvesting, grading, packaging, and transportation due to reasons such as collision, compression, and vibration. Not only does this reduce the external appearance quality of fruits and vegetables, but it also makes them susceptible to fungal or bacterial invasion, leading to rotting (such as late blight, dry rot, soft rot, etc.), affecting their edible safety.

Currently, relevant technologies utilize optical detection techniques to inspect the surface of fruits and vegetables. Optical detection techniques typically use multiple cameras to image the fruits. Subsequently, the obtained images undergo manual calibration and stitching to obtain an image of the fruit surface. This method results in the issue of misalignment in the stitched image, causing an incomplete display of the entire image of the fruit surface. As a result, it becomes challenging to precisely locate and identify defects on the fruit surface, posing difficulties in subsequent fruit sorting tasks and leading to a decrease in sorting accuracy.

SUMMARY

In view of this, the present disclosure provides a detection system, method, computer device, and computer-readable storage medium to obtain a complete surface image of the measured object. This serves as the foundation for the precise localization and identification of surface defects in subsequent processes.

The technical solutions of the present disclosure are implemented as follows.

The present disclosure, in some embodiments, provides a detection system comprising a laser, a camera unit, and a computer device. The camera unit is mounted in an upper region of the measured object, the laser is mounted directly above the measured object, and an emission port of the laser is directly facing the measured object. The laser is configured to project a laser plane, and the laser plane intersects a surface of the measured object to form laser lines, wherein the laser lines divide the surface into multiple distinct regions of interest. The camera unit is configured to capture images of the measured object from different shooting angles, wherein each image comprises a portion or the entirety of each region of interest. The computer device is configured to segment and stitch all the images based on the regions of interest comprised in each image, thereby obtaining the target image of the surface.

In the embodiments of the present disclosure, calibration of the surface of the measured object is achieved through the laser, which divides the surface into distinct regions of interest. The camera unit then captures images from various shooting angles. As the laser lines divide non-overlapping regions on the surface, the computer device can analyze the proportion of each region of interest in every image. This allows for image stitching, thus obtaining a complete surface image of the measured object. Therefore, precise localization and identification of surface defects in subsequent steps are ensured.

Optionally, the computer device can be specifically configured for segmenting the to-be-processed image to obtain multiple segmented images based on the position of the laser lines in the to-be-processed image, wherein the to-be-processed image is any one of all the images; selecting a segmented image with a maximum proportion of the region of interest from the multiple segmented images as an image to be stitched corresponding to the to-be-processed image; traversing all the images to obtain the image to be stitched corresponding to each image; and according to a predetermined reference coordinate system, unfolding and stitching each image to be stitched to obtain the target image.

In the embodiments of the present disclosure, obtaining a complete surface image of the measured object enhances the accuracy of locating and identifying surface defects.

Optionally, the camera unit can include at least one camera, and when multiple cameras are present, the multiple cameras can be mounted side by side.

In the embodiments of the present disclosure, arranging multiple cameras side by side can help avoid coordinate alignment issues caused by different camera orientations, thereby reducing the difficulty of subsequent image processing.

Optionally, one group of camera unit can be provided, and the camera unit can be moved to different shooting positions to capture images from various shooting angles.

In the embodiments of the present disclosure, moving one camera unit to different shooting positions for capturing surface image provides more reference information about the surface image of the measured object. This enhances the accuracy of subsequent image stitching.

Optionally, the camera unit can be in three groups, namely the first camera unit, the second camera unit, and the third camera unit. The first camera unit can be located directly above the measured object, and the direction of view of the first camera unit can be parallel to the laser. Angles between a normal of the second camera unit and a normal of the first camera unit and between a normal of the third camera unit and a normal of the first camera unit can be the same.

In the embodiments of the present disclosure, capturing surface images using multiple camera units provides more reference information for obtaining a complete surface image of the measured object. This enhances the accuracy of subsequent image stitching.

Optionally, a range of values for the angle can be from 30 degrees to 50 degrees.

Optionally, the value for the angles can be 40 degrees.

In the embodiments of the present disclosure, controlling the above-mentioned angle within a reasonable range helps avoid issues of excessive overlap or missing in the shooting regions of multiple camera units due to too small or too large angle, thereby improving the accuracy of subsequent image stitching.

Optionally, at least one laser can be provided, and when there are two lasers, the two lasers can be distributed on both sides of the first camera unit.

In the embodiments of the present disclosure, using multiple lasers allows for a finer division of the surface region of the measured object, thus enhancing the accuracy of subsequent image stitching.

Optionally, a width of the laser lines can be less than 2 millimeters.

In the embodiments of the present disclosure, controlling the width of the laser lines within a reasonable range can avoid situations where the laser lines covering small defects on the surface of the target object result in an inability to accurately capture all defects on the surface of the target object.

Optionally, the detection system can also include a rotation device; and the rotation device can be configured to drive the measured object to rotate.

Optionally, the rotation device can be composed of a cup, a bracket, and a cup wheel. The cup can contain the measured object, the bracket can support the cup, and the cup wheel can be located in a middle of the bracket. The cup wheel can rotate around an axis of the cup, thereby driving the measured object to rotate.

In the embodiments of the present disclosure, it is possible to detect various surfaces of the measured object in real time, thus providing more surface information for accurate localization and identification of surface defects.

Optionally, the detection system can also include a conveyor belt. The conveyor belt can make contact with the cup wheel of the rotation device, and the conveyor belt can move circularly under motor drive. The friction between the conveyor belt and the cup wheel can drive the rotation of the cup wheel, thereby causing the measured object to rotate.

In the embodiments of the present disclosure, it can be beneficial for detecting various surfaces of the measured object in real time, thus providing more surface information for accurate localization and identification of surface defects.

Optionally, the measured object can be an object of a circular shape or an elliptical shape.

In the embodiments of the present disclosure, the smooth curves of the surfaces of objects with circular shape or elliptical shape result in smooth laser lines formed on the surface. This allows for a uniform division of the surface and reduces the difficulty of subsequent image processing.

In some other embodiments of the present disclosure, a detection method is provided. The detection method can include capturing images of the measured object acquired by the camera unit at different shooting angles, wherein each image comprises a portion or the entirety of each region of interest; and the region of interest is formed by segmenting by laser lines formed by intersecting between a laser plane projected by a laser located in a region directly above the measured object and a surface of the measured object; and segmenting and stitching all the images based on the regions of interest present in each image, thereby obtaining the target image of the surface.

In the embodiments of the present disclosure, calibration of the surface of the measured object is achieved through the laser, which divides the surface into distinct regions of interest. The camera unit then captures images from various shooting angles. Because the laser lines divide the surface into non-overlapping regions, it is possible to perform image stitching by the proportion of regions of interest in each image. This enables the acquisition of a complete surface image of the measured object. Therefore, precise localization and identification of surface defects in subsequent steps are ensured.

Optionally, the step of segmenting and stitching all the images based on the regions of interest present in each image, thereby obtaining the target image of the surface can comprise segmenting the to-be-processed image to obtain multiple segmented images based on the position of the laser lines in the to-be-processed image, wherein the to-be-processed image is any one of all the images; selecting a segmented image with a maximum proportion of the region of interest from the multiple segmented images as an image to be stitched corresponding to the to-be-processed image; traversing all the images to obtain the image to be stitched corresponding to each image; and according to a predetermined reference coordinate system, unfolding and stitching each image to be stitched to obtain the target image.

In the embodiments of the present disclosure, obtaining a complete surface image of the measured object enhances the accuracy of locating and identifying surface defects.

In some more embodiments, the present disclosure provides a computer device comprising a processor and memory. The memory can store a computer program executable by the processor. The processor is capable of executing the computer program to implement the detection method described in the embodiments of the present disclosure.

In some more embodiments, the present disclosure provides a computer-readable storage medium. The computer-readable storage medium can store a computer program. When executed by a processor, the computer program implements the detection method as described in the embodiments of the present disclosure.

The present disclosure provides a detection system, method, computer device, and computer-readable storage medium. The detection system can comprise a laser, a camera unit, and a computer device. The camera unit is mounted in an upper region of the measured object, the laser is mounted directly above the measured object, and an emission port of the laser is directly facing the measured object. The laser is configured to project a laser plane, and the laser plane intersects a surface of the measured object to form laser lines, wherein the laser lines divide the surface into multiple distinct regions of interest. The camera unit is configured to capture images of the measured object from different shooting angles, wherein each image comprises a portion or the entirety of each region of interest. The computer device is configured to segment and stitch all the images based on the regions of interest comprised in each image, thereby obtaining the target image of the surface. The distinction from related technologies is that related optical detection technology uses manual calibration and stitching for the obtained images. However, the obtained surface images are unaligned, with missing or overlapping regions, causing an incomplete display of the entire image of the fruit surface. As a result, it becomes challenging to precisely locate and identify defects on the fruit surface, posing difficulties in subsequent fruit sorting tasks and leading to a decrease in sorting accuracy. In the present disclosure, calibration of the surface of the measured object is achieved through the laser, and the laser lines divide the surface into distinct regions of interest. The camera unit then captures images from various shooting angles. As the laser lines divide non-overlapping regions on the surface, the computer device can analyze the proportion of each region of interest in every image. This allows for image stitching, thus obtaining a complete surface image of the measured object. Therefore, precise localization and identification of surface defects in subsequent steps are ensured.

BRIEF DESCRIPTION OF DRAWINGS

To more clearly illustrate the technical solutions of the embodiments of the present disclosure, the following will briefly introduce the drawings used in the embodiments. It should be understood that the following drawings only show some embodiments of the present disclosure, and therefore they should not be regarded as a limitation on the scope. Those ordinary skilled in the art can also obtain other related drawings based on these drawings without inventive effort.

DETAILED DESCRIPTION OF EMBODIMENTS

Figure 1:
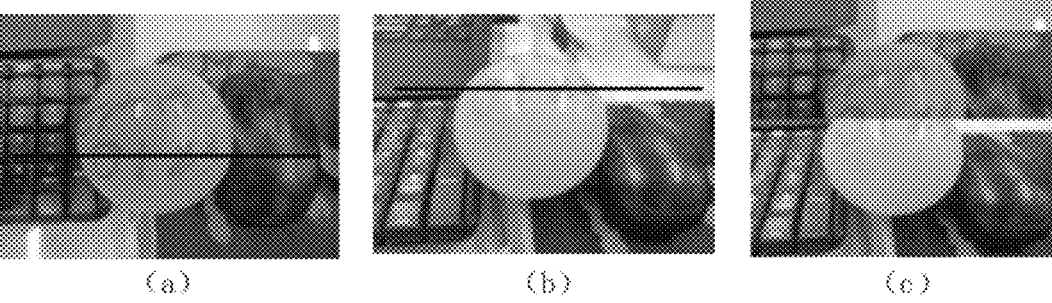
FIG. 1 is a schematic diagram of a related optical fruit detection technology.

In order to make the objective, technical solutions, and advantages of the embodiments of the present disclosure clearer, the following description will provide a clear and comprehensive explanation of the technical solutions in the embodiments of the present disclosure with reference to the drawings. Clearly, the described embodiments are part of the embodiments of the present disclosure and not the entire embodiments. The components of embodiments of the present disclosure which are generally described and illustrated in the drawings herein can be arranged and designed in a variety of different configurations.

Accordingly, the following detailed description of the embodiments of the present disclosure provided in the drawings is not intended to limit the scope of the claimed disclosure but merely represents selected embodiments of the present disclosure. Based on the embodiments in the present disclosure, all other embodiments obtained by those of ordinary skill in the art without making inventive efforts are within the scope of protection of the present disclosure.

It should be noted that similar numerals and letters denote similar terms in the following drawings, so that once an item is defined in one drawing, it does not need to be further discussed in subsequent drawings.

In the description of the present disclosure, it should be noted that the orientation or position relationships indicated by the terms "up", "down", "inside", "outside", etc. are the orientation or position relationships shown based on the drawings or the orientation or position relationships customarily placed in the use of the product of the present disclosure. It is only for the convenience of describing the present disclosure and simplifying its description and does not indicate or imply that the device or element referred to must be in a specific orientation or be constructed and operated in a specific orientation, and thus should not be construed as limiting the present disclosure.

In addition, the terms such as "first" and "second", are only used to distinguish the descriptive and are not to be construed as indicating or implying relative importance.

It should be noted that the features in the embodiments of the present disclosure may be combined with each other without conflict.

Currently, for the accurate localization and identification of surface defects on fruits, relevant technologies utilize optical detection techniques to inspect the surface of fruits and vegetables. Optical detection techniques typically use multiple cameras to image the fruits. Subsequently, the obtained images undergo manual calibration and stitching to obtain an image of the fruit surface. A specific implementation is shown in FIG. 1. FIG. 1 is a schematic diagram of a related optical fruit detection technology.

The related optical fruit detection technology uses multiple cameras to capture surface images of fruits. For example, in some possible embodiments, one camera is arranged directly above the measured object, and then one camera is arranged on each side of that camera. These cameras simultaneously capture images of the fruit. The captured images are represented as (a) and (b) in FIG. 1, and then integration is performed manually to obtain the fruit surface image shown in (c) in FIG. 1.

As shown in (a) in FIG. 1, image processing personnel first manually determine calibration lines (black straight lines in the figure) in both (a) and (b) in FIG. 1. Subsequently, based on the calibration line in (a) (black straight line in the figure), the image is segmented, and the image region above the black line is retained. In (b) in FIG. 1, image processing personnel perform segmentation on (b) based on the black straight line in FIG. 1, and the image region below the black line is retained. Subsequently, the retained portions of the images cropped from (a) and (b) are stitched together to obtain the image shown in (c) in FIG. 1. It can be seen that the obtained surface images are unaligned, with missing or overlapping regions, thus causing an incomplete display of the entire image of the fruit surface. As a result, it becomes challenging to precisely locate and identify defects on the fruit surface, posing difficulties in subsequent fruit sorting tasks and leading to a decrease in sorting accuracy.

Figure 2:
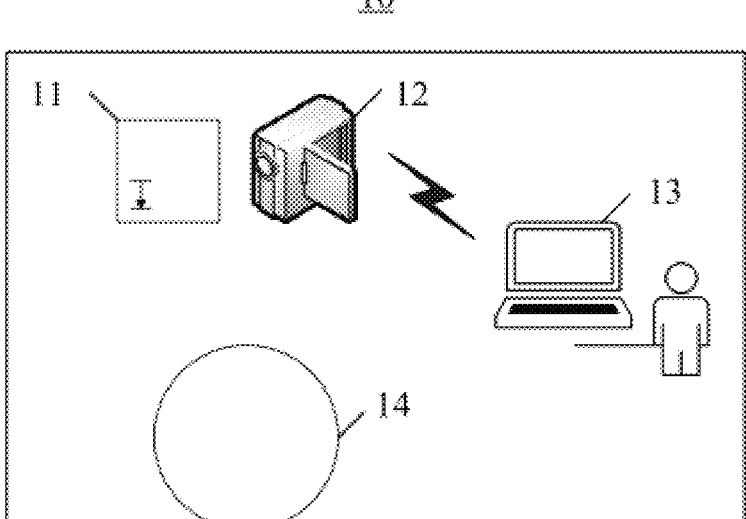
FIG. 2 is an architectural diagram of a detection system provided in the embodiments of the present disclosure.

In order to solve the above technical problems, the embodiments of the present disclosure provide a detection system. Referring to FIG. 2, FIG. 2 is an architectural diagram of a detection system provided in the embodiments of the present disclosure, and the detection system 10 can comprise a laser 11, a camera unit 12, and a computer device 13.

The camera unit 12 can be mounted in an upper region of the measured object 14; the laser 11 can be mounted directly above the measured object 14; and an emission port of the laser 11 can be directly facing the measured object 14.

The laser 11 can be configured to project a laser plane, and the laser plane can intersect a surface of the measured object 14 to form laser lines, wherein the laser lines can divide the surface into multiple distinct regions of interest.

In the embodiments of the present disclosure, the aforementioned regions of interest refer to the non-overlapping regions on two sides of the laser lines on the surface of the measured object. In the images captured by the camera unit, the regions of interest can be the visible regions of the measured object in the image.

The camera unit 12 can be configured to capture images of the measured object 14 from different shooting angles, wherein each image can comprise a portion or the entirety of each region of interest.

The computer device 13 can be configured to segment and stitch all the images based on the regions of interest comprised in each image, thereby obtaining the target image of the surface.

The distinction from related technologies is that related optical detection technology uses manual calibration and stitching for the obtained images. However, the obtained surface images are unaligned, with missing or overlapping regions, causing an incomplete display or reduplicated display of the entire image of the fruit surface. As a result, it becomes challenging to precisely locate and identify defects on the fruit surface, posing difficulties in subsequent fruit sorting tasks and leading to a decrease in sorting accuracy. In the present disclosure, calibration of the surface of the measured object is achieved through the laser, and the laser lines divide the surface into distinct regions of interest. The camera unit then captures images from various shooting angles. As the laser lines divide non-overlapping regions on the surface, the computer device can analyze the proportion of each region of interest in every image. This allows for image stitching, thus obtaining a complete surface image of the measured object. Therefore, precise localization and identification of surface defects in subsequent steps are ensured.

Figure 3:
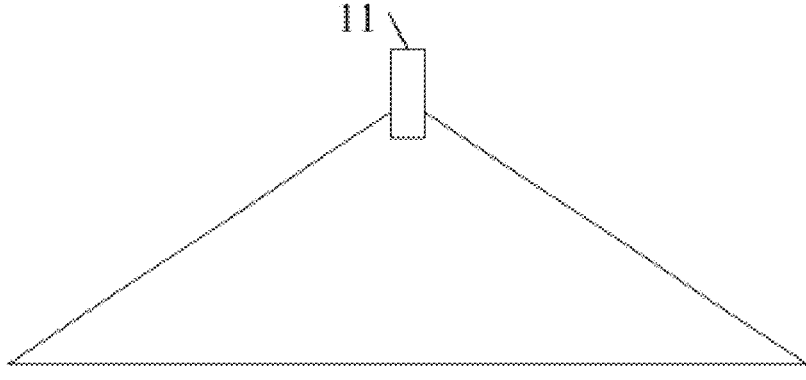
FIG. 3 is a schematic diagram of a laser plane projected by a laser.

Optionally, the aforementioned laser 11 can be, but is not limited to, a linear laser generator. The laser 11 can emit a fan-shaped laser in one direction. As shown in FIG. 3, FIG. 3 is a schematic diagram of a laser plane projected by a laser.

Figure 4:
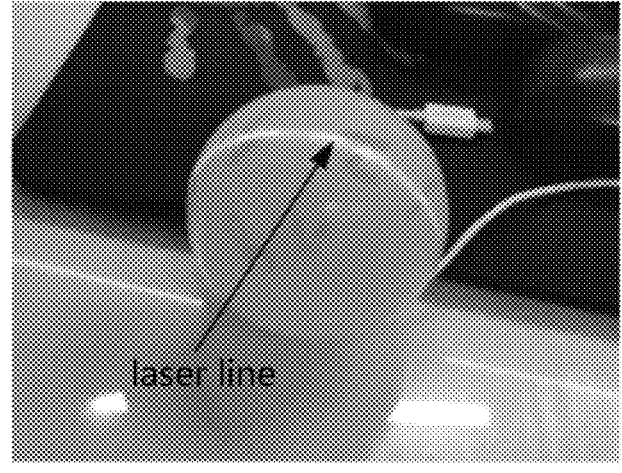
FIG. 4 is a schematic diagram of laser lines provided in the embodiments of the present disclosure.

In the embodiments of the present disclosure, the emission port of the laser 11 is directly facing the measured object 14. Hence, the laser plane projected by laser 11 can form a laser line when intersecting with the surface of the measured object 14. The laser line can divide the surface of the measured object 14 into multiple distinct regions of interest. For ease of understanding, referring to FIG. 4, FIG. 4 is a schematic diagram of laser lines provided in the embodiments of the present disclosure, with the laser line positioned as shown in FIG. 4.

In a preferred embodiment, a width of the laser lines above can be less than 2 millimeters.

Understandably, when the laser line diverges upon emission and has an excessive width, upon irradiation onto the surface of the target object, the laser line occupies a larger area of the surface of the target object. This can lead to situations where the laser lines covering small defects on the surface of the target object result in an inability to accurately capture all defects on the surface of the target object. It is foreseeable that the width of the laser line has a more significant impact on smaller fruits. The smaller the fruit is, the narrower the laser line width should be.

Figure 5:
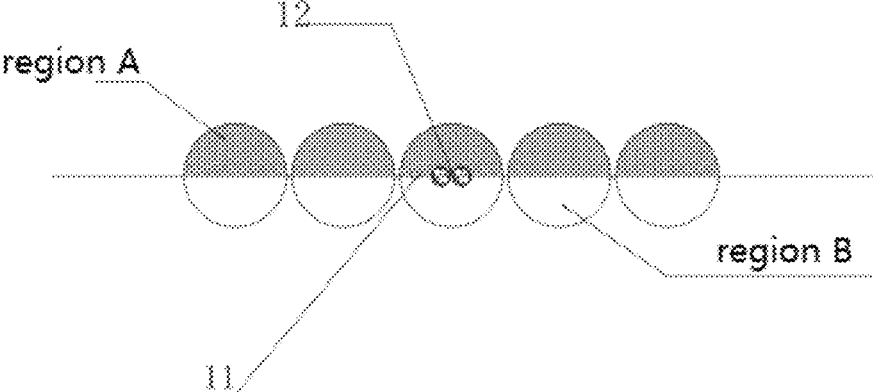
FIG. 5 is a schematic diagram of a region of interest provided in the embodiments of the present disclosure.

Understandably, the aforementioned region of interest refers to the regions on both sides of the laser line. For clarity, an example is given by the shooting angle of a camera unit arranged directly above the measured object 14. A schematic diagram of the region of interest is provided. FIG. 5 is a schematic diagram of a region of interest provided in the embodiments of the present disclosure.

As can be seen, both the camera unit 12 and the laser 11 are arranged directly above the measured object. The laser line divides the measured object into two regions of interest, namely, region A and region B. It is evident that the images captured by the camera unit directly above the measured object 14 comprise the entirety of region A and region B. If the camera unit is at a certain angle with the normal direction of the measured object, the images captured by the camera unit can comprise only a portion of region A and region B.

It is also understandable that when there is one laser 11, the surface of the measured object 14 can be divided into two regions of interest. If there are at least two lasers, then the surface of the measured object 14 can be divided into multiple regions of interest. In other words, the number of regions of interest is equal to the number of lasers plus one. It is foreseeable that the more lasers there are, the finer the surface of the measured object is divided. This can enhance the accuracy of subsequent image stitching.

Optionally, the aforementioned camera unit 12 can include, but is not limited to, one camera. In some scenarios, when there are multiple cameras within the camera unit 12, the multiple cameras are arranged in a parallel mounting manner. The multiple cameras can simultaneously capture the same surface image of the measured object, providing more image resources for determining the surface image. This facilitates precise localization and identification of surface defects in subsequent processes.

In some possible embodiments, the above-mentioned camera unit 12 can be in one group, and the camera unit 12 can be moved to different shooting positions to capture images from various shooting angles.

It should be noted that when one camera unit is used for image capture, the measured object 14 is in a stationary state so as to allow the camera unit to capture the same surface image of the measured object 14 from different angles.

Figure 6:
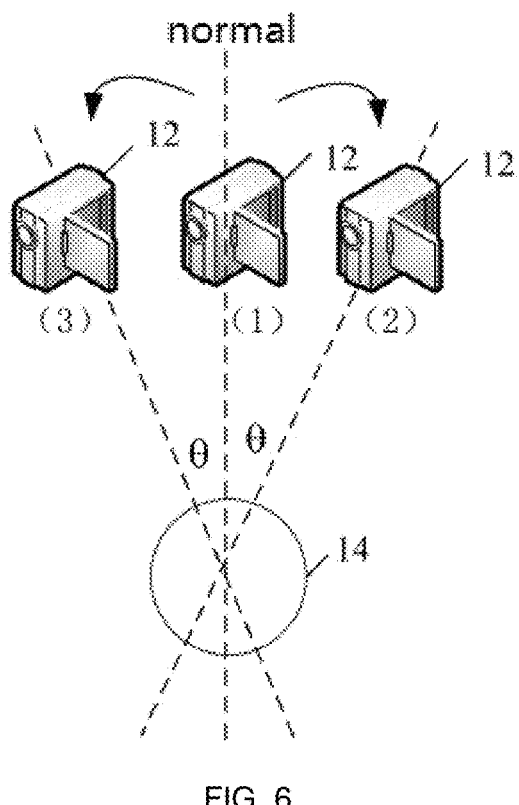
FIG. 6 is a schematic diagram of the measured object captured using a camera unit in the embodiments of the present disclosure.

For example, referring to FIG. 6, FIG. 6 is a schematic diagram of the measured object captured using a camera unit in the embodiments of the present disclosure. As shown in FIG. 6, assuming the initial position (1) of the camera assembly 12 is directly above the measured object 14, after the camera unit 12 captures the image from directly above, the camera assembly 12 can be controlled to move clockwise by a preset angle θ (such as 40 degrees, or any angle within the range of 30 to 50 degrees) to reach position (2). After capturing the image at the shooting angle, the camera unit 12 is controlled to move counterclockwise by the preset angle θ back to position (1). Then the camera unit 12 continues to move counterclockwise by the preset angle θ to reach position (3) and captures images at this shooting position. After completing the capture at position (3), the camera unit 12 is controlled to move clockwise by the preset angle θ back to the initial position (1). Therefore, the surface image capture of the measured object 14 is completed.

It should be noted that the initial mounting position of the above camera unit 12 can be implemented in various ways, and it is not limited here.

Continuing with FIG. 6, in the process of using a camera unit 12 for image capture, in the first scenario, the initial position of the camera unit 12 can be the position (1) in FIG. 6, and the process of changing the shooting position is as described above. In the second scenario, the initial position of the camera unit 12 can also be the position (2) shown in FIG. 6. In this case, the shooting process would be as follows. After capturing an image at position (2), the camera unit is controlled to move counterclockwise by the preset angle θ to reach position (1). After completing the capture at position (1), the camera unit 12 is controlled to move counterclockwise by the preset angle θ to reach position (3) for shooting. In the third scenario, the initial position of the camera unit 12 can also be the position (3) shown in FIG. 6. In this case, the shooting process would be as follows. After capturing an image at position (3), the camera unit is controlled to move clockwise by the preset angle θ to reach position (1). After completing the capture at position (1), the camera unit 12 is controlled to move clockwise by the preset angle θ to reach position (2) for shooting.

In another preferred embodiment, the aforementioned camera unit 12 can be in three groups, namely the first camera unit 121, the second camera unit 122, and the third camera unit 123, with fixed mounting positions for the three camera units.

It should be noted that when three camera units are used for image capture, the measured object 14 is in a stationary state. The three camera units can start shooting simultaneously to ensure that the three camera units capture the same surface image of the measured object at the same time.

Figure 7:
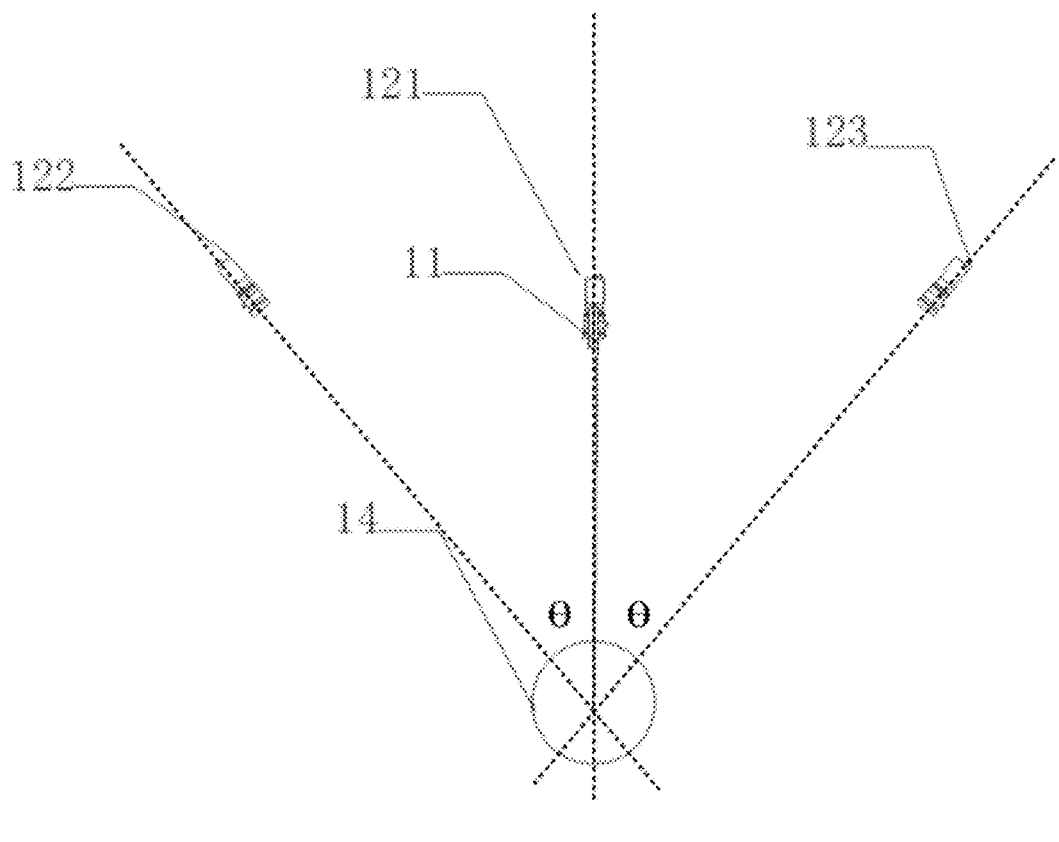
FIG. 7 is a schematic diagram of the implementation of three camera units provided in the embodiments of the present disclosure.

Exemplarily, a schematic diagram of the mounting position of the three camera units can be seen in FIG. 7. FIG. 7 is a schematic diagram of the implementation of three camera units provided in the embodiments of the present disclosure.

As shown in FIG. 7, the first camera unit 121 can be located directly above the measured object 14, and the direction of view of the first camera unit can be parallel to the laser. Angles between a normal of the second camera unit 122 and a normal of the first camera unit 121 and between a normal of the third camera unit 123 and a normal of the first camera unit 121 can be the same. Additionally, the aforementioned normal can be perpendicular to the shooting plane of the camera unit.

In some possible embodiments, if the angle of the aforementioned angle is too small or too large, there may be an issue with excessive overlapping region or missing between the shooting regions of the second camera unit 122 and the third camera unit 123 and the shooting region of the first camera unit 121. Therefore, the range of values for the aforementioned angle is from 30 degrees to 50 degrees, and in a preferred embodiment, the aforementioned angle is preferably 40 degrees.

Figure 8:
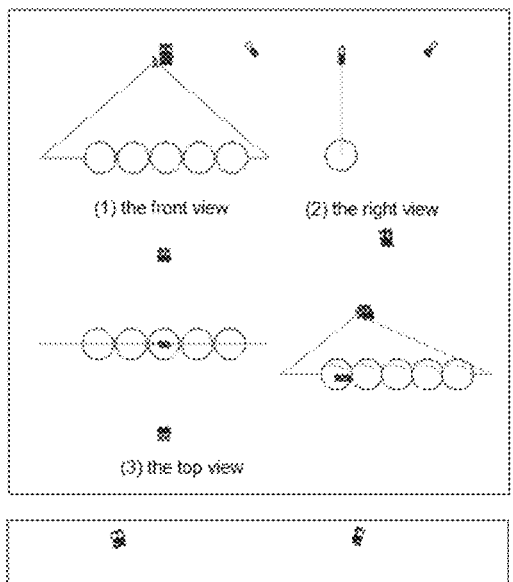
FIG. 8 is a three-view diagram of a detection system with a single laser provided in the embodiments of the present disclosure.
Figure 8:
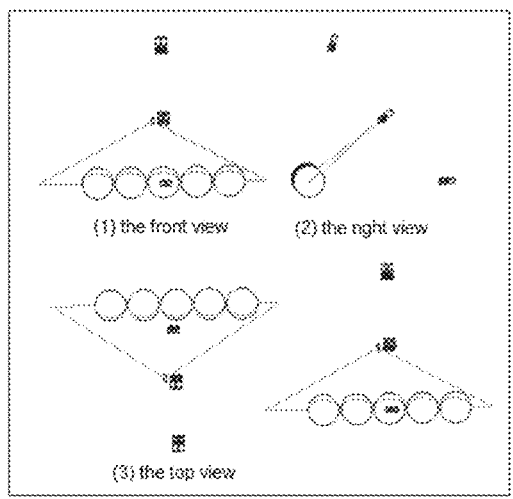
Figure 8:
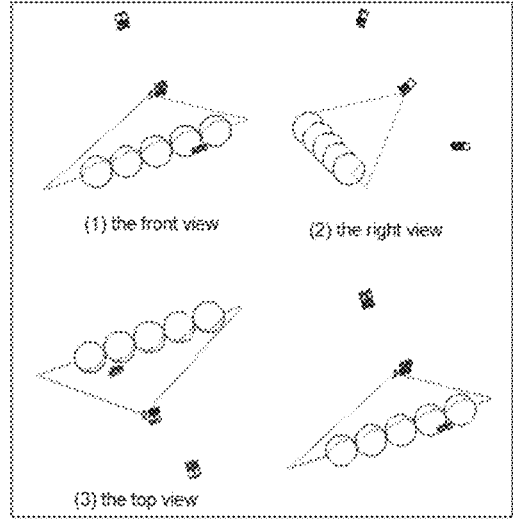
Figure 8:
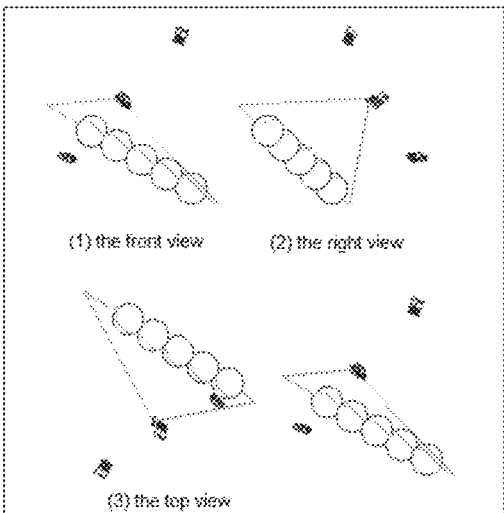
Figure 9A:
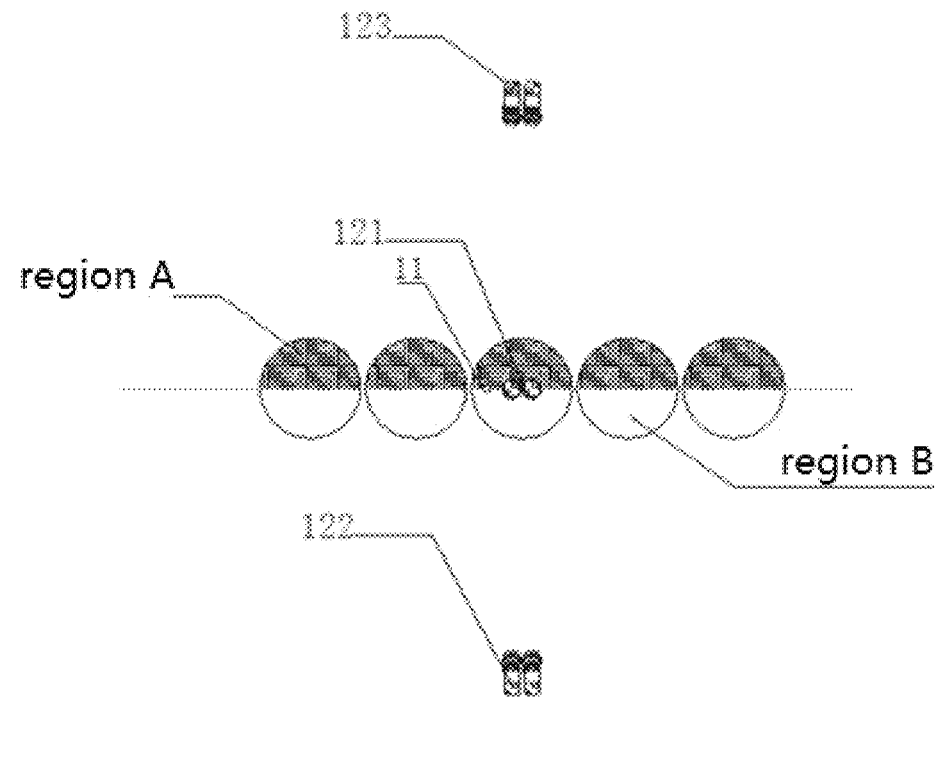
FIGS. 9A to 9C are schematic diagrams of shooting angles for three camera units provided in the embodiments of the present disclosure.
Figure 9B:
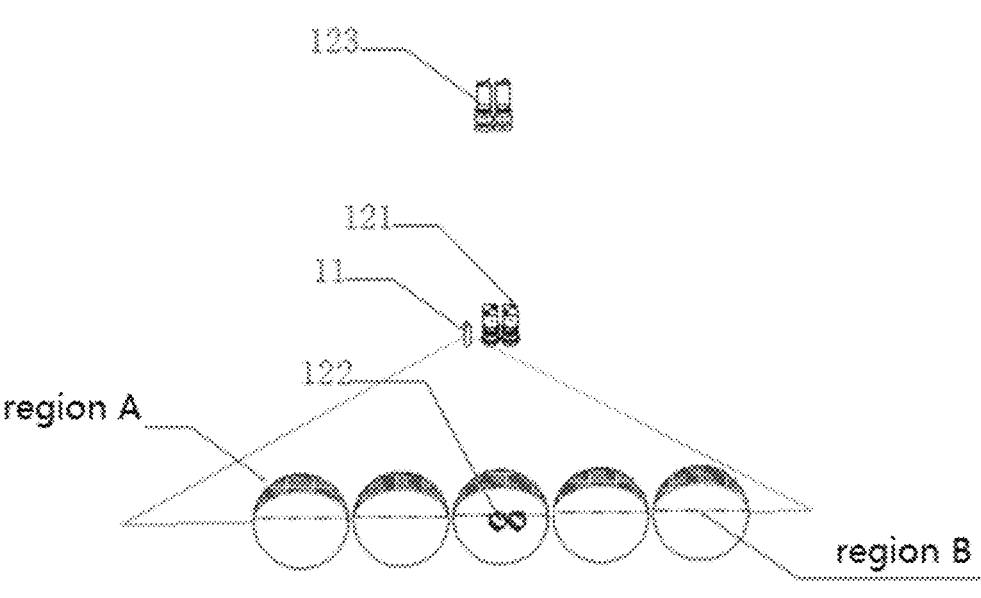
Figure 9C:
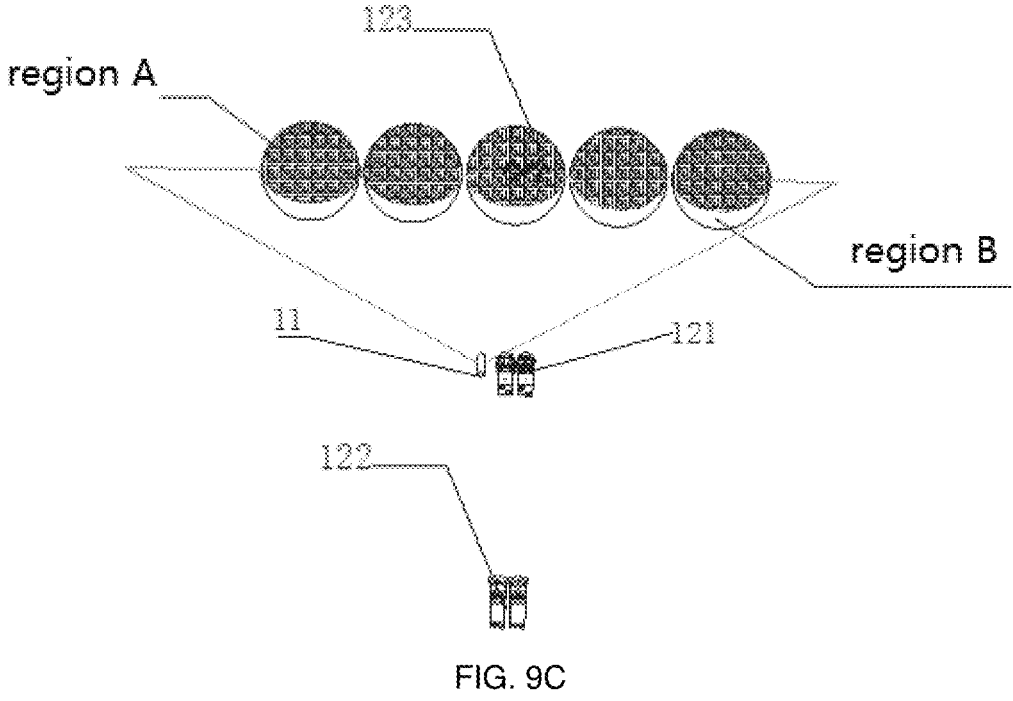

As an example, when there are three camera units, the overall view of the entire detection system can be as shown in FIG. 8. Referring to FIG. 8, FIG. 8 is a three-view diagram of a detection system with a single laser provided in the embodiments of the present disclosure. It includes (1) the front view, (2) the right view, and (3) the top view. In conjunction with the three views shown in FIG. 8, the schematic diagrams of the shooting angles for each camera unit are provided below in reference to FIG. 8. Referring to FIGS. 9A to 9C, FIGS. 9A to 9C are schematic diagrams of shooting angles for three camera units provided in the embodiments of the present disclosure. In the FIGS. 9A to 9C, a laser 11 is provided. The laser line divides the measured object 14 into two regions of interest, namely, region A and region B.

Firstly, taking the shooting angle of the first camera unit 121 as an example in FIG. 9A, it can be observed that the shooting range of the first camera unit 121 can include the entire region A and the entire region B. In other words, the images captured by the first camera unit 121 comprise the entirety of region A and region B.

Optionally, in FIG. 9B at the shooting angle of the second camera unit 122, the shooting range of the second camera unit 122 can include some of region A and some of region B. The part of region A included can be smaller than the part of region B included. In other words, the image captured by the second camera unit 122 can include a portion of region A and a portion of region B, wherein the portion of region A can be smaller than the portion of region B.

Optionally, in FIG. 9C at the shooting angle of the third camera unit 123, the shooting range of the third camera unit 123 can also include some of region A and some of region B. The part of region A included can be greater than the part of region B included. In other words, the image captured by the third camera unit 123 can include a portion of region A and a portion of region B, wherein the portion of region A can be greater than the portion of region B.

For ease of understanding, an example is given by assuming the image from the first camera unit 121 includes the entire region A and entire region B, which can be represented as 100% of region A and 100% of region B included. The image from the second camera unit 122 includes 30% of region A and 70% of region B, and the image from the third camera unit 123 includes 70% of region A and 30% of region B. In the process of determining the target image, the most ideal reference regions would be 70% of region B from the image of the second camera unit 122 and 70% of region A from the image of the third camera unit 123.

It should be noted that to maximize the inclusion of the surface information of the target object in the field of view of the three camera units, there can be an overlap in the target surface information captured by the three camera units. In order to locate overlap regions and ensure the uniqueness of the image information for the first camera unit 121, the second camera unit 122, and the third camera unit 123, a laser 11 can be mounted near the position of the first camera unit 121.

It should be noted that in the embodiments of the present disclosure, capturing images of the measured object from different angles with three camera units can achieve the effect of obtaining a complete surface image. It can be anticipated that the technical results achieved with four or more camera units should be similar to the technical results achieved with three camera units.

In some possible embodiments, at least one laser 11 can be provided, and when there are two lasers 11, the two lasers can be distributed on both sides of the first camera unit 121. Both lasers 11 can be parallel to the first camera unit 121.

Figure 10:
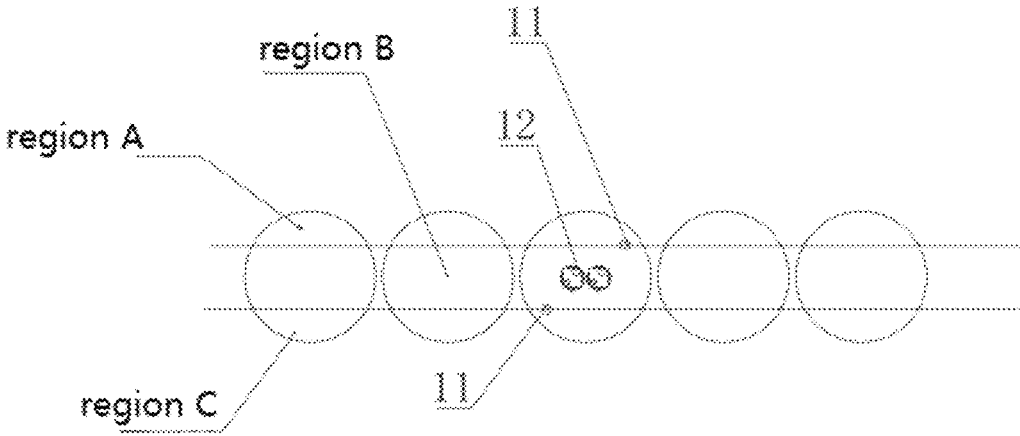
FIG. 10 is a schematic diagram of another region of interest provided in the embodiments of the present disclosure.

Exemplarily, when two lasers are present, an example is given by the shooting angle of a camera unit arranged directly above the measured object 14. A schematic diagram of the region of interest is provided. FIG. 10 is a schematic diagram of another region of interest provided in the embodiments of the present disclosure.

As shown in FIG. 10, two laser lines can be formed on the surface of the measured object 14. The measured object is divided into three regions of interest: region A, region B, and region C. Obviously, the images captured by camera unit 12 include the entirety of region A, region B, and region C. If the camera unit 12 is at a certain angle with the normal direction of the measured object 14, the images captured by the camera unit 12 can comprise a portion of the region A, a portion of the region B, and a portion of the region C.

Figure 11:
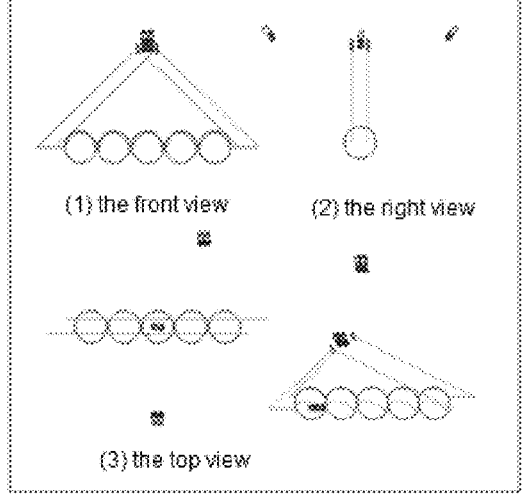
FIG. 11 is a three-view diagram of a detection system with two lasers provided in the embodiments of the present disclosure.
Figure 11:
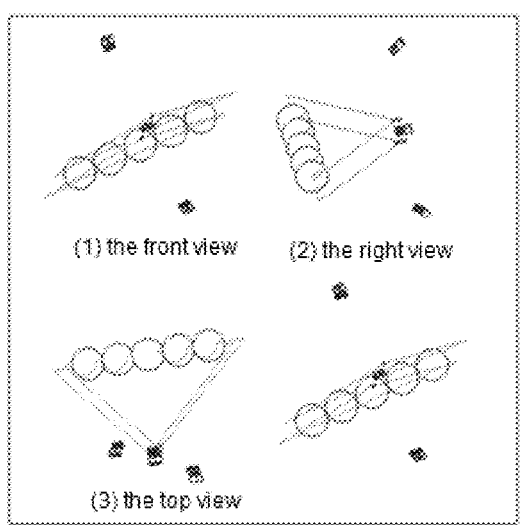
Figure 11:
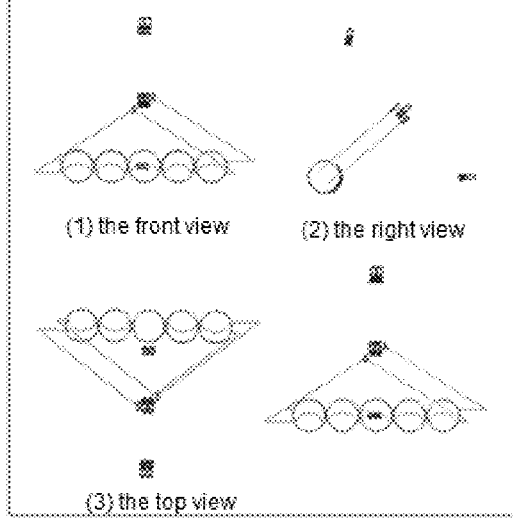
Figure 11:
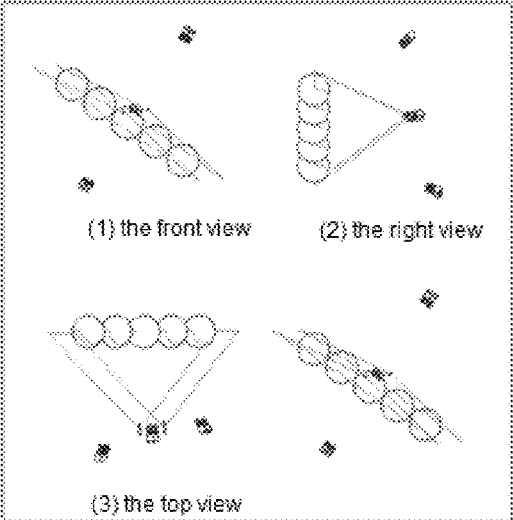

Based on FIG. 8, a three-view view of a detection system comprising two lasers is also given below. Referring to FIG. 11, FIG. 11 is a three-view diagram of a detection system with two lasers provided in the embodiments of the present disclosure. It includes (1) the front view, (2) the right view, and (3) the top view.

Exemplarily, in conjunction with FIGS. 10 and 11, firstly, an example is given by the shooting angle of the first camera unit 121. it can be observed that the shooting range of the first camera unit 121 can include the entire region A, the entire region B, and the entire region C. At the shooting angle of the second camera unit 122, the shooting range of the second camera unit 122 can include part of region A, part of region B, and part of region C. At the shooting angle of the third camera unit 123, the shooting range of the third camera unit 123 can also include part of region A and part of region B. In one possible embodiment, the image from the first camera unit 121 can include 100% of region A, 100% of region B, and 100% of region C. Then, the image from the second camera unit 122 can include 10% of region A, 30% of region B, and 60% of region C; and the image from the third camera unit 123 may contain 60% of region A, 30% of region B, and 60% of region C. In the process of determining the target image, the ideal reference regions would be 100% of region B from the first camera unit, 60% of region C from the image of the second camera unit 122, and 60% of region A from the image of the third camera unit 123.

Optionally, to ultimately obtain a complete surface image, the computer device 13 shown in FIG. 1 can be configured for segmenting the to-be-processed image to obtain multiple segmented images based on the position of the laser lines in the to-be-processed image, wherein the to-be-processed image is any one of all the images; and selecting a segmented image with a maximum proportion of the region of interest from the multiple segmented images as an image to be stitched corresponding to the to-be-processed image.

For example, continuing with the above example, the image from the second camera unit 122 includes 30% of region A and 70% of region B, and the image from the third camera unit 123 includes 70% of region A and 30% of region B. So, in the to-be-processed image captured by the second camera unit, the image region including 70% of region B will be selected as the image to be stitched. Similarly, in the to-be-processed image captured by the third camera unit, the image region including 70% of region A will be selected as the image to be stitched.

Therefore, the image to be stitched corresponding to each image is obtained by traversing all the images. According to a predetermined reference coordinate system, each image to be stitched is unfolded and stitched to obtain the target image.

Figure 12:
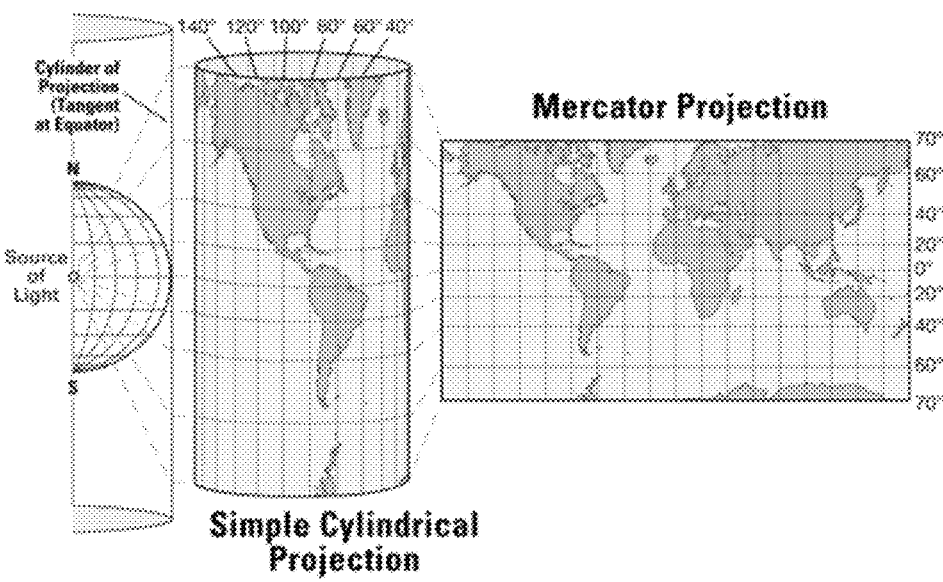
FIG. 12 is a schematic diagram of a reference coordinate system provided in the embodiments of the present disclosure.

In some possible embodiments, the aforementioned predetermined reference coordinate system can be represented as the schematic diagram of the reference coordinate system shown in FIG. 12. The image processing program can unfold the image to be stitched with reference to the position calibrated by the laser line in a manner similar to latitude and longitude lines on a globe.

It should be noted that in the scenario where there is one laser, the images captured by the second camera unit 122 and the third camera unit 123 can be stitched and processed, and the images captured by the first camera unit 121 are not involved in the image stitching process. In the scenario where there are two lasers, the images captured by the first camera unit 121, the second camera unit 122, and the third camera unit 123 all need to be involved in the image stitching process. For the images captured by the first camera unit 121 and the second camera unit 122, the segmented image with the maximum percentage of the region of interest is selected for stitching. In the case of the first camera unit 121, the segmented image including the middle region of interest is selected for image stitching.

Optionally, to ensure the acquisition of all surface information of the measured object, the detection system in the various embodiments mentioned above can also include a rotation device. The rotation device is configured to drive the measured object to rotate, thus allowing the camera unit to capture images of various surfaces in real time. This can enhance the accuracy of subsequent positioning and identifying surface defects, providing higher precision for subsequent sorting tasks.

In one possible embodiment, the aforementioned rotation device can be composed of a cup, a bracket, and a cup wheel. The cup can contain the measured object, the bracket can support the cup, and the cup wheel can be located in a middle of the bracket. The cup wheel can rotate around an axis of the cup, thereby driving the measured object to rotate so as to ensure 360° detection of the measured object without dead angle.

Figure 13:
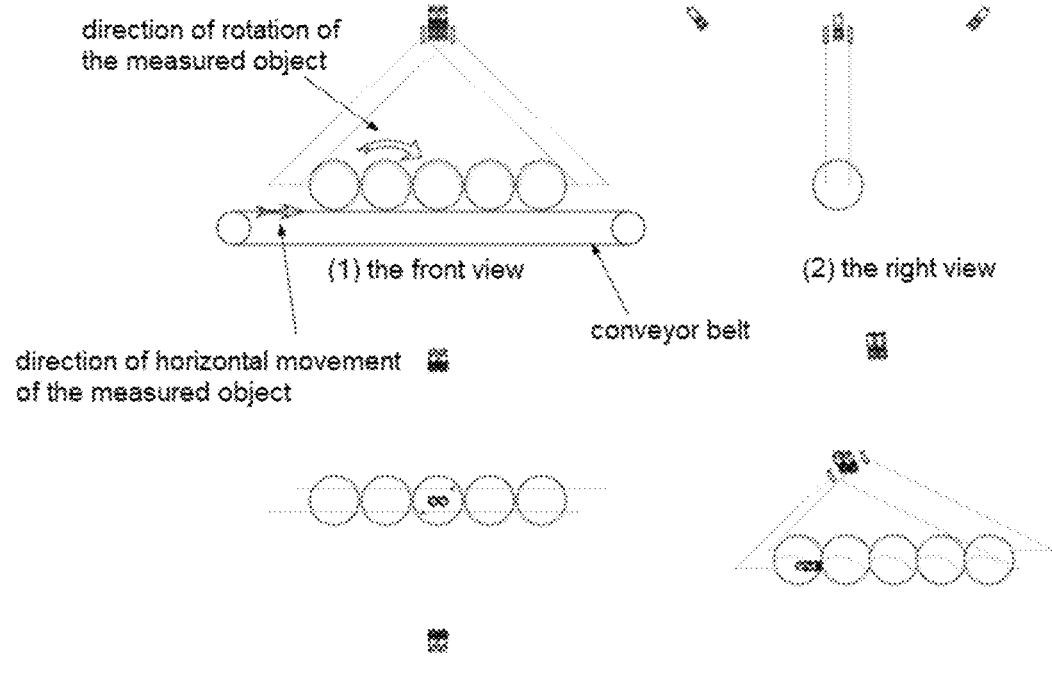
FIG. 13 is a three-view diagram of another detection system provided in the embodiments of the present disclosure.

In some possible embodiments, to drive the rotation of the rotation device, the above-mentioned detection system can also include a conveyor belt. Referring to FIG. 13, FIG. 13 is a three-view diagram of another detection system provided in the embodiments of the present disclosure, where the measured object in the figure is placed in the cup of the rotation device (the rotation device is omitted in FIG. 13). The conveying direction of the conveyor belt can be the same as the rotation direction of the cup wheel. The cup wheel of the rotation device can make contact with the conveyor belt, and the conveyor belt can move circularly under motor drive. The friction between the conveyor belt and the cup wheel can drive the rotation of the cup wheel, thereby causing the object to rotate.

Optionally, the measured object in the various embodiments mentioned above can be, but is not limited to, a circular or elliptical object. For example, the measured object can be, but is not limited to, fruits or vegetables.

In the embodiments of the present disclosure, the smooth curves of the surfaces of objects with circular shapes or elliptical shapes result in smooth laser lines formed on the surface. This allows for a uniform division of the surface and reduces the difficulty of subsequent image processing.

Figure 14:
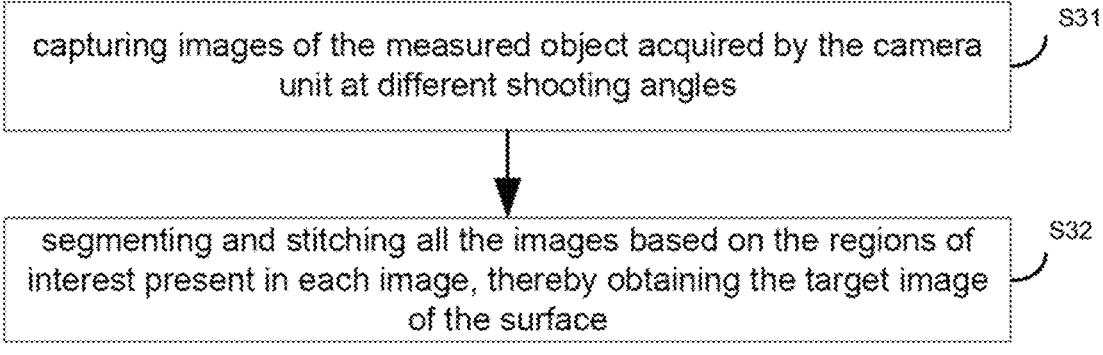
FIG. 14 is a schematic flowchart of a detection method provided in the embodiments of the present disclosure.

Based on the same inventive concept, the embodiments of the present disclosure also provide a detection method that can be applied to the computer device shown in FIG. 1. Referring to FIG. 14, FIG. 14 is a schematic flowchart of a detection method provided in the embodiments of the present disclosure. The method can include the following steps.

S31: capturing images of the measured object acquired by the camera unit at different shooting angles, wherein each image comprises a portion or the entirety of each region of interest; and the region of interest is formed by segmenting by laser lines formed by intersecting between a laser plane projected by a laser located in a region directly above the measured object and a surface of the measured object.

S32: segmenting and stitching all the images based on the regions of interest present in each image, thereby obtaining the target image of the surface.

Optionally, in a possible embodiment, the above step S32 can include the following sub-steps.

Sub-step 321: segmenting the to-be-processed image to obtain multiple segmented images based on the position of the laser lines in the to-be-processed image, wherein the to-be-processed image is any one of all the images.

Sub-step 322: selecting a segmented image with a maximum proportion of the region of interest from the multiple segmented images as an image to be stitched corresponding to the to-be-processed image.

Sub-step 323: traversing all the images to obtain the image to be stitched corresponding to each image.

Sub-step 324: according to a predetermined reference coordinate system, unfolding and stitching each image to be stitched to obtain the target image.

To implement the steps of the detection method in the above embodiments, an implementation of a detection device is given below. It should be noted that the detection device provided in the present embodiment has the same basic principle and produces the same technical effect as the above-described embodiment, and for the objective of a brief description, the corresponding contents in the above-described embodiment may be referred to where not mentioned in the present embodiment portion. The detection device can comprise an acquisition module, which can be configured for capturing images of the measured object acquired by the camera unit at different shooting angles, wherein each image comprises a portion or the entirety of each region of interest; and the region of interest is formed by segmenting by laser lines formed by intersecting between a laser plane projected by a laser located in a region directly above the measured object and a surface of the measured object; and a processing module, which can be configured for segmenting and stitching all the images based on the regions of interest present in each image, thereby obtaining the target image of the surface.

Optionally, the processing module can be specifically configured for segmenting the to-be-processed image to obtain multiple segmented images based on the position of the laser lines in the to-be-processed image, wherein the to-be-processed image is any one of all the images; selecting a segmented image with a maximum proportion of the region of interest from the multiple segmented images as an image to be stitched corresponding to the to-be-processed image; traversing all the images to obtain the image to be stitched corresponding to each image; and according to a predetermined reference coordinate system, unfolding and stitching each image to be stitched to obtain the target image.

Figure 15:
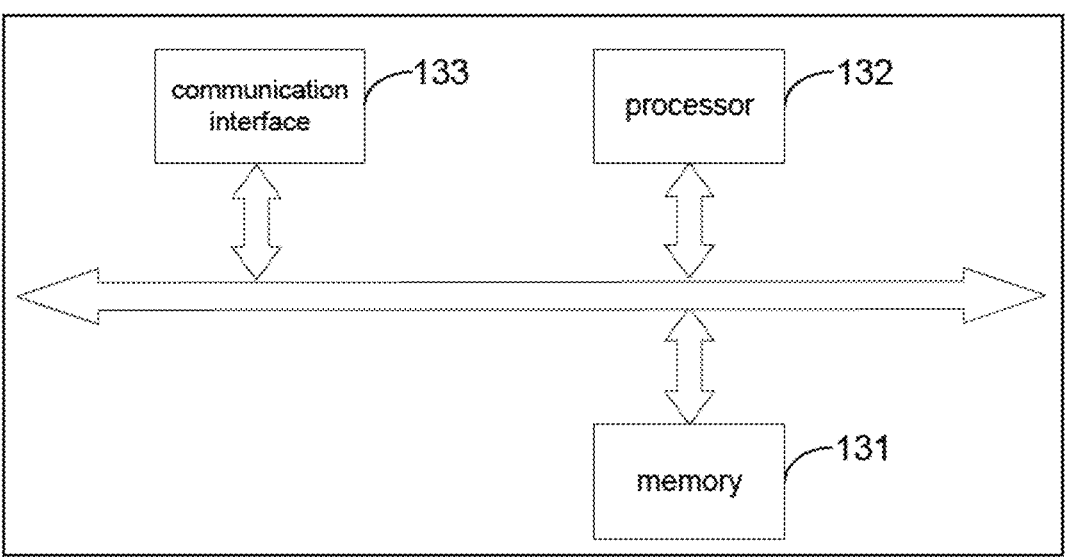
FIG. 15 is a structural block diagram of a computer device provided in the embodiments of the present disclosure.

The embodiments of the present disclosure also provide a computer device, as in FIG. 15. FIG. 15 is a structural diagram of a computer device provided in the embodiments of the present disclosure. The computer device 13 can include a communication interface 131, a processor 132, and a memory 133. The processor 132, memory 133, and communication interface 131 can be electrically connected to each other directly or indirectly to facilitate data transfer or interaction. For example, these components can be electrically connected to each other through one or more communication buses or signal lines. The memory 133 can be configured to store software programs and modules, such as the program instructions/modules corresponding to the detection method provided in the embodiments of the present disclosure. The processor 132 can execute the software programs and modules stored in memory 133 to perform various functional applications and data processing. The communication interface 131 can be configured for the communication of signals or data with other nodes or devices. In the present disclosure, the computer device 130 can have multiple communication interfaces 131.

The memory 133 can be, but is not limited to, random access memory (RAM), read only memory (ROM), programmable read-only memory (PROM), erasable programmable read-only memory (EPROM), electrically erasable programmable read-only memory (EEPROM), and the like.

The processor 132 can be an integrated circuit chip with signal processing capability. The processor can be a general-purpose processor, comprising a central processing unit (CPU), network processor (NP), etc. It can also be a digital signal processor (DSP), application specific integrated circuit (ASIC), field-programmable gate array (FPGA), or other programmable logic devices, discrete gates, or transistor logic devices, as well as discrete hardware components.

Optionally, the modules mentioned above can be stored in the memory shown in FIG. 15 in the form of software or firmware and can be embedded in the operating system (OS) of the computer device, executable by the processor depicted in FIG. 15. At the same time, the data, program code, and other elements required for executing the above modules can be stored in the memory.

The embodiments of the present disclosure provide a computer-readable storage medium on which computer programs can be stored. When executed by a processor, the programs can implement any of the detection methods described in the aforementioned embodiments. The computer-readable storage medium can be, but is not limited to, USB drives, external hard drives, ROM, RAM, PROM, EPROM, EEPROM, magnetic disks, optical discs and other various media capable of storing program code.

The above is only a specific embodiment of the present disclosure, but the scope of protection of the present disclosure is not limited thereto. Any person skilled in the art can easily envisage changes or substitutions within the technical scope disclosed in the present disclosure, which should be encompassed within the scope of protection of the present disclosure. Therefore, the scope of protection of the present disclosure shall be stated to be subject to the scope of protection of the claims.

INDUSTRIAL PRACTICALITY

The present disclosure discloses a detection system, method, computer device, and computer-readable storage medium. The detection system comprises a laser, a camera unit, and a computer device. The camera unit is mounted in an upper region of the measured object, the laser is mounted directly above the measured object, and an emission port of the laser is directly facing the measured object. The laser is configured to project a laser plane, and the laser plane intersects a surface of the measured object to form laser lines, wherein the laser lines divide the surface into multiple distinct regions of interest. The camera unit is configured to capture images of the measured object from different shooting angles, wherein each image comprises a portion or the entirety of each region of interest. The computer device is configured to segment and stitch all the images based on the regions of interest comprised in each image, thereby obtaining the target image of the surface. The present disclosure is able to obtain the complete stitched surface image. Therefore, precise localization and identification of surface defect positions in subsequent steps are ensured.

Additionally, it can be understood that the detection system, method, computer device, and computer-readable storage medium of the present disclosure are reproducible and can be applied in various industrial applications. For example, the detection system of the present disclosure can be applied in the field of detection.

What is claimed is:

1. A detection system, comprising a laser, a camera unit, and a computer device, wherein the camera unit is mounted in an upper region of a measured object, the laser is mounted directly above the measured object, and an emission port of the laser is directly facing the measured object;

the laser is configured to project a laser plane, and the laser plane intersects a surface of the measured object to form laser lines, wherein the laser lines divide the surface into multiple distinct regions of interest;

the camera unit is configured to capture images of the measured object from different shooting angles, wherein each image comprises a portion or an entirety of each region of interest; and the computer device is configured to segment and stitch all the images based on regions of interest comprised in each image, thereby obtaining a target image of the surface, wherein the computer device is configured for segmenting a to-be-processed image to obtain multiple segmented images based on a position of the laser lines in the to-be-processed image, wherein the to-be-processed image is any one of all the images;

selecting a segmented image with a maximum proportion of the regions of interest from the multiple segmented images as an image to be stitched corresponding to the to-be-processed image;

traversing all the images to obtain the image to be stitched corresponding to each image; and according to a predetermined reference coordinate system, unfolding and stitching each image to be stitched to obtain the target image.

2. The detection system according to claim 1, wherein the camera unit comprises at least one camera, and when multiple cameras are present, the multiple cameras are mounted side by side.

3. The detection system according to claim 1, wherein one group of the camera unit is provided, and the camera unit is moved to different shooting positions to capture images from various shooting angles.

4. The detection system according to claim 1, wherein a width of the laser lines is less than 2 millimeters.

5. The detection system according to claim 1, wherein the measured object is an object of a circular shape or an elliptical shape.

6. The detection system according to claim 1, wherein the detection system further comprises a rotation device; and the rotation device is configured to drive the measured object to rotate.

7. The detection system according to claim 6, wherein the rotation device is composed of a cup, a bracket, and a cup wheel, wherein the cup contains the measured object, the bracket supports the cup, and the cup wheel is located in a middle of the bracket; and the cup wheel rotates around an axis of the cup, thereby driving the measured object to rotate.

8. The detection system according to claim 7, wherein the detection system further comprises a conveyor belt; the conveyor belt makes contact with the cup wheel of the rotation device, and the conveyor belt moves circularly under motor drive; and a friction between the conveyor belt and the cup wheel drives rotation of the cup wheel, thereby causing the measured object to rotate.

9. The detection system according to claim 1, wherein three groups of the camera unit are provided, namely the first camera unit, the second camera unit, and the third camera unit;

the first camera unit is located directly above the measured object, and a direction of view of the first camera unit is parallel to the laser; and an angle between a normal of the second camera unit and a normal of the first camera unit and an angle between a normal of the third camera unit and the normal of the first camera unit are the same.

10. The detection system according to claim 9, wherein the angle is 40 degrees.

11. The detection system according to claim 9, wherein at least one laser is provided, and when two lasers are provided, the two lasers are distributed on both sides of the first camera unit.

12. The detection system according to claim 9, wherein a range of values for the angle is from 30 degrees to 50 degrees.

13. The detection system according to claim 12, wherein at least one laser is provided, and when two lasers are provided, the two lasers are distributed on both sides of the first camera unit.

14. A detection method, wherein the detection method comprises capturing images of a measured object acquired by a camera unit at different shooting angles, wherein each image comprises a portion or an entirety of each region of interest; and the region of interest is formed by segmenting by laser lines formed by intersecting between a laser plane projected by a laser located in a region directly above the measured object and a surface of the measured object; and segmenting and stitching all the images based on the region of interest present in each image, thereby obtaining a target image of the surface;

wherein the step of segmenting and stitching all the images based on the region of interest present in each image, thereby obtaining a target image of the surface, comprises segmenting a to-be-processed image to obtain multiple segmented images based on a position of the laser lines in the to-be-processed image, wherein the to-be-processed image is any one of all the images;

selecting a segmented image with a maximum proportion of the region of interest from the multiple segmented images as an image to be stitched corresponding to the to-be-processed image;

traversing all the images to obtain the image to be stitched corresponding to each image; and according to a predetermined reference coordinate system, unfolding and stitching each image to be stitched to obtain the target image.

15. A computer device, comprising a processor and a memory, wherein the memory stores computer instructions capable of being executed by the processor, and the processor executes the computer instructions to implement the detection method according to claim 14.

* * * * *